(12) United States Patent
diGirolamo (10) Patent No.: US 8,423,300 B1
(45) Date of Patent: Apr. 16, 2013

(54) METHOD AND SYSTEM FOR MONITORING THE STRUCTURAL INTEGRITY OF STRUCTURAL MEMBERS OF A BUILDING

(75) Inventor: Edward G. diGirolamo, Raleigh, NC (US)

(73) Assignee: The Steel Network, Inc., Durham, NC (US)

( * ) Notice: Subject to any disclaimer, the term of this patent is extended or adjusted under 35 U.S.C. 154(b) by 257 days.

(21) Appl. No.: 12/776,497

(22) Filed: May 10, 2010

(51) Int. Cl.
*G01B 3/44* (2006.01)
*G06F 19/00* (2011.01)

(52) U.S. Cl.
USPC .............................................. 702/34; 324/700

(58) Field of Classification Search ............... 702/34, 702/35; 324/699, 700; 73/862.041; 340/539.13, 340/572.1
See application file for complete search history.

(56) References Cited

U.S. PATENT DOCUMENTS

| | | | |
|---|---|---|---|
| 6,690,182 B2 * | 2/2004 | Kelly et al. ................... | 324/700 |
| 7,012,520 B2 | 3/2006 | Webb, Sr. | |
| 7,434,480 B2 | 10/2008 | Georgeson et al. | |
| 7,474,217 B2 | 1/2009 | Himberger et al. | |

OTHER PUBLICATIONS

"INGECOM launches low-cost active tag", RFIDNews; http://www.rfidnews.org/2009/03/26/ingecom-launches-low-cost-active-tag; 1 page, Mar. 26, 2009.
"Roads Bridges and RFID"; http://www.rfid-rnet.com/Presentasjoner_12_mars_2008/workshop%2012%20March%202008%200.%20Vermesan%20M.%20Viktil%20SINTEF.pdf; 1 page, Mar. 12, 2008.
Cheng, et al.; "An Introduction for Mega House"; 25th International Symposium on Automation and Robotics in Construction; Jun. 26-29, 2008; p. 52; http://www.iaarc.org/external/isarc2008-cd/www/3/3_sec_009_Cheng_et_al_An_introduction.pdf, Jun. 26-29, 2008

* cited by examiner

*Primary Examiner* — John H Le
(74) *Attorney, Agent, or Firm* — Coats & Bennett, PLLC (57) ABSTRACT

A system for monitoring the structural integrity of structural members of a building using radio frequency identification tags. A plurality of radio frequency modules are secured to structural members, each module including a radio frequency identification tag, a micro processor, a first memory, one or more sensors for measuring data related to the structural integrity of the building members and a transceiver for receiving operational instructions used to monitor the structural integrity of the building and for transmitting the measured data. There is also provided a computing system that transmits the operational instructions to the radio frequency modules and receives the measured data from the modules. In addition, the computing system stores the measured data in a second memory and processes the measured data from the modules.

18 Claims, 9 Drawing Sheets

METHOD AND SYSTEM FOR MONITORING THE STRUCTURAL INTEGRITY OF STRUCTURAL MEMBERS OF A BUILDING

FIELD ON INVENTION

The present invention relates generally to monitoring the structural integrity of structural members of a building using radio-frequency identification tags with associated sensors.

BACKGROUND

With the aging of many of the structures built within the last 50 years, it is becoming more and more important for property managers to be able to monitor the structural integrity in order to maintain acceptable levels of safety. Current methods, usually a simple visual inspection, are insufficient for accurate assessment of the structural integrity since most of the real indicators of a potential failure are not easily assessable via visual inspection. For example, it is not possible to determine if the stress on a particular support member is changing over time with a visual inspection. In addition, even if a person conducting the inspection could see the stress changes over time, most of the support members are not readily accessible for visual inspection.

Further, catastrophic events such as fire, weather or explosions can cause structural integrity failures. First responders are currently also limited to visual inspection to determine structural integrity. They have no way of knowing the status of interior support members. This could lead to improper decisions and could result in loss of time and potentially increase the risk of injury to the persons entering the structure.

SUMMARY OF INVENTION

The present invention relates to monitoring the structural integrity of buildings using radio-frequency modules secured to metal clips which are attached to various structural members throughout the building. Along with a unique radio-frequency identification (RFID) tag number, data about the structural integrity of the building is measured using sensors connected to the radio-frequency modules and stored in memory for future processing. Once initialized and activated, a remote computing system is utilized to issue operating instructions to the radio-frequency modules and to receive the measured data from each of the modules using wireless communication protocols, such as a wireless local area network (WLAN) protocol, or a cellular mobile telephone system. In addition, the computing system used to monitor the structural integrity is capable of correlating the RFID tag number with each metal clip to a location in the building, comparing the measured data to a set of previously saved data to determine if a change in structural integrity has occurred, and incorporate the comparison result into a three-dimensional model for displaying the structural integrity of the building via a user interface.

DETAILED DESCRIPTION

Referring now to the drawings, the present invention will be described in the context of monitoring the structural integrity of a building. Those skilled in the art will appreciate, however, that the present invention may be applied to other apparatus where the structural members are required to be monitored, such as aircraft, bridges and other forms of infrastructure.

Figure 1:
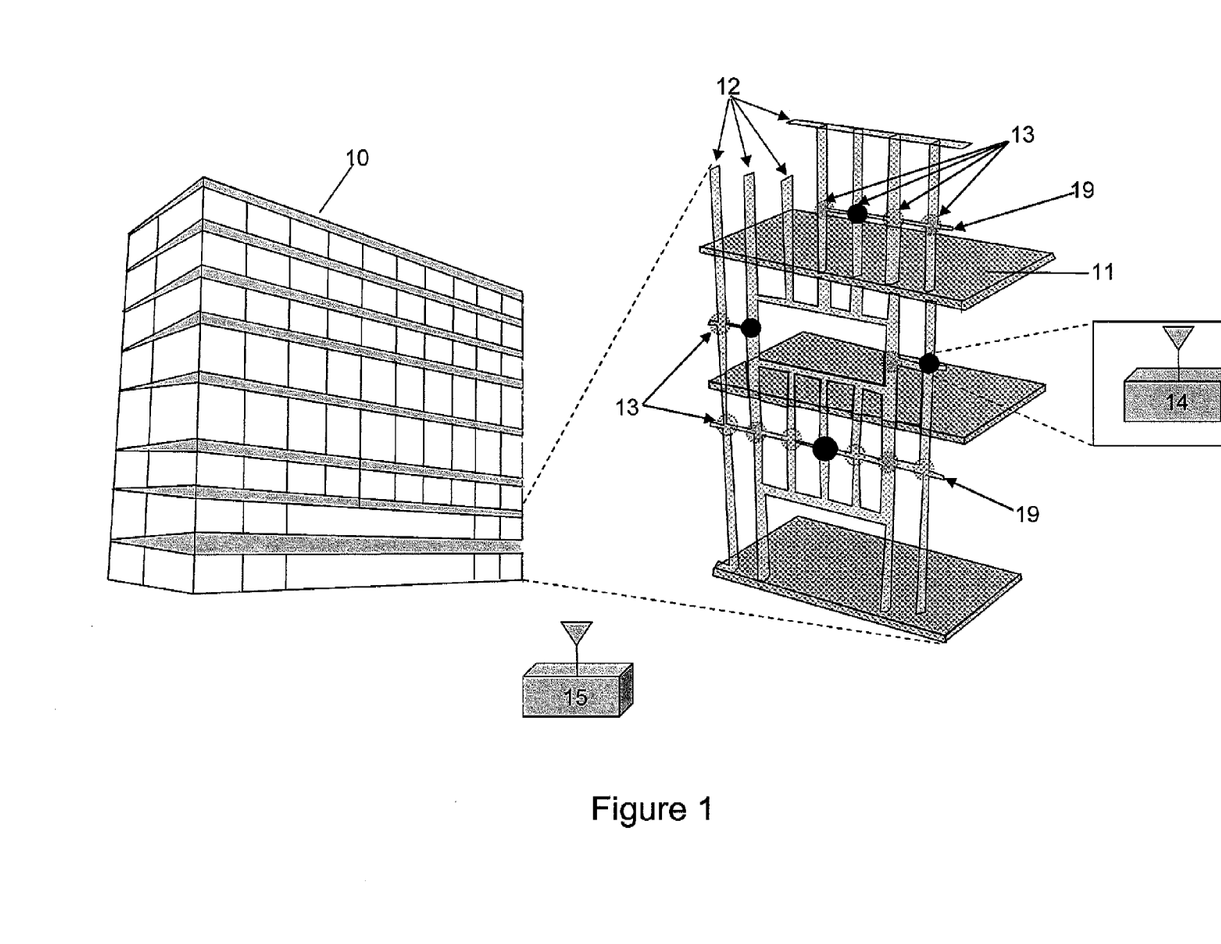
FIG. 1 is a perspective view of a building model and a preferred embodiment of the present invention.

As shown in FIG. 1, an exemplary illustration of a building 10 to be monitored is provided. Building 10 is constructed using horizontal concrete pads 11 and vertical walls made of structural members 12. The structural members 12 are usually metal studs which are typically pre-fabricated at a separate production facility. Structural members 12 do not have to be metal, but could be made of other materials which have similar structural properties. The pre-fabricated members are delivered to the construction site where they are placed in position based on architectural drawings or blueprints. Structural members 12 are attached to concrete pads 11 to form the different levels within building 10.

Figure 2:
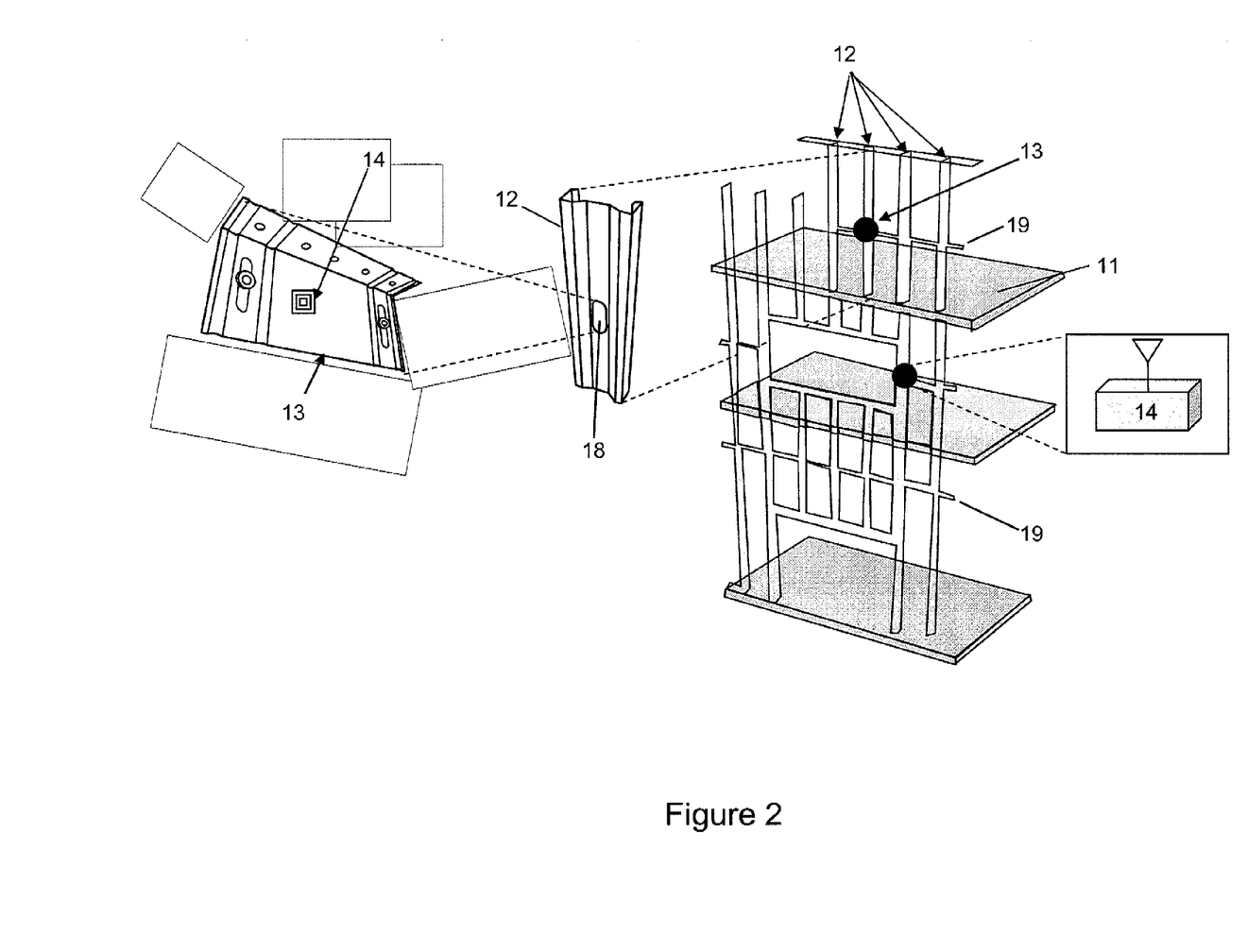
FIG. 2 is a cross-section view of structural member of the building with radio-frequency modules secured to metal clips.

Turning to FIG. 2, in addition to attaching the structural members to concrete pads 11, multiple structural members 12 are secured together by placing a bridging member 19 through pre-fabricated holes 18 within the structural members 12. This ensures proper alignment of the structural members and provides an increase in load bearing potential of the vertical walls of the structural members 12. Each bridging member 19 is attached to the multiple structural members 12 using metal clips 13. Metal clips 13 are attached to the bridging members 19 and the respective structural members 12. The clips 13 may be constructed of materials other than metal. For example, the clips 13 may be constructed of a composite material or plastic.

After, or even during, construction it may be desired to monitor the structural integrity of structural members 12 and/or concrete pads 11 to ensure that there are no unexpected stresses or failures. In one illustrative example, information necessary to report the structural integrity of structural members 12 is measured and stored using radio-frequency modules (RFMs) 14, which are secured to respective metal clips 13. Once initialized and activated, a remote computing system 15 can be used to issue operating instructions to the RFMs 14 and to receive data from each of the modules 14 using wireless communication protocols, such as a wireless local area network (WLAN) protocol, a cellular mobile telephone system, or any type of proxy based system.

Figure 3A:
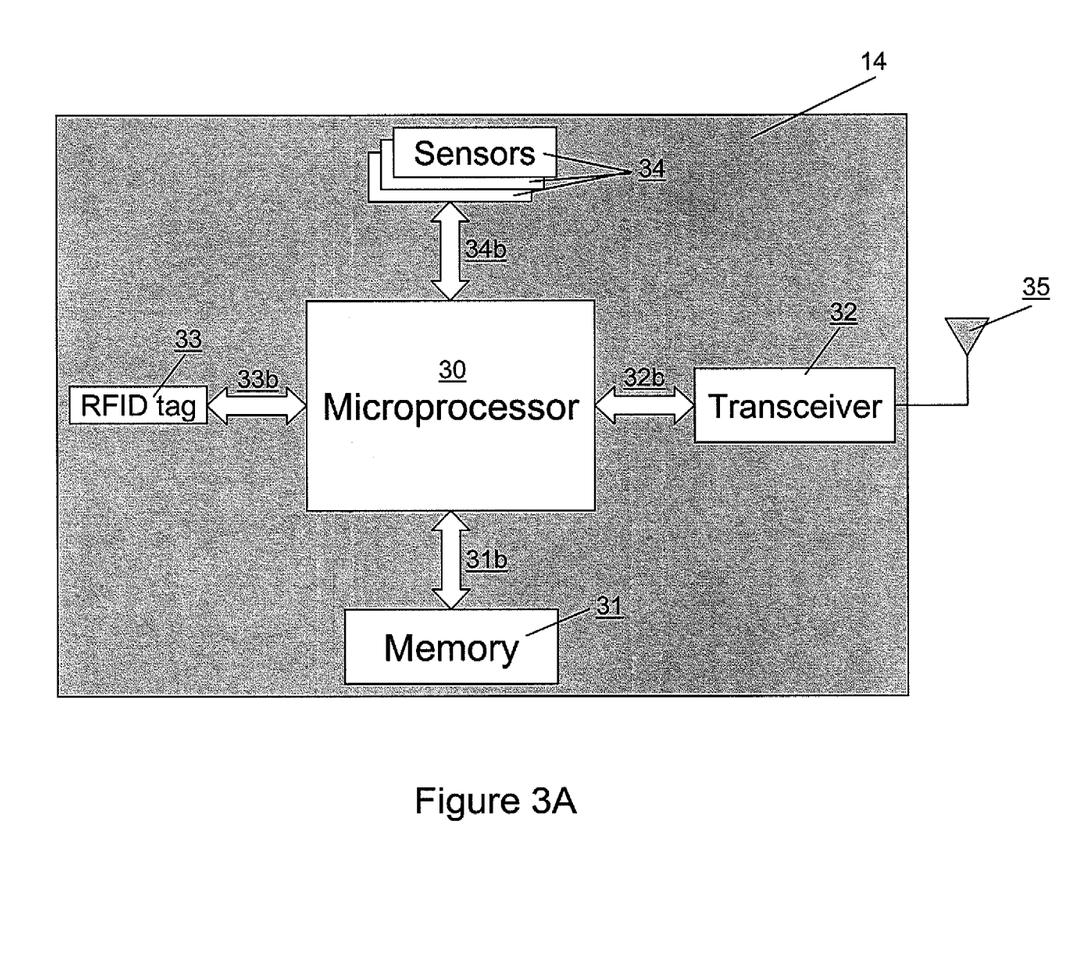
FIG. 3A illustrates an exemplary radio-frequency module.

FIG. 3A illustrates a block diagram of an exemplary RFM 14. RFM 14 includes one or more sensors 34 for measuring data related to the structural integrity of structural members 12 of building 10. One or more sensors 34 could measure any number of different parameters and can include temperature sensors, strain gauges, pressure sensors, torque sensors or any number of different types of sensors necessary to evaluate structural integrity. RFM 14 also includes microprocessor 30, radio-frequency identification (RFID) tag 33, module memory 31, and module transceiver 32.

Microprocessor 30 is operatively connected to module memory 31 via memory bus 31b. Module memory 31 can store various measurement results from one or more sensors 34, but could also contain operational instructions used by microprocessor 30. Measured data from one or more sensors 34 is provided to microprocessor 30 via sensor bus 34b. Microprocessor 30 can perform any necessary processing to the measured data, such as data compression, correlating and formatting. The processed data is then sent to module memory 31 via memory bus 31b for storage. However, it should be understood that the measured data from one or more sensors 34 could be sent directly to module memory 31 without microprocessor 30 performing any processing.

In addition, microprocessor 30 is used to control all the functionality and timing of the radio-frequency module 14. For example, when computing system 15 requests RFM 14 to provide measured data. In response to the request, microprocessor 30 reads the stored data from module memory 31 and appends the measured data to RFID tag 33 for encoding. The processed data is encoded using methods known in the art and provided (via transceiver bus 32b) to module transceiver 32. Module transceiver 32 amplifies the encoded data and transmits the encoded data to computing system 15.

The amount of amplification necessary to ensure that the encoded data is correctly transmitted to computing system 15 is determined using techniques known in the wireless telecommunication arts. For example, microprocessor 30 could also contain circuitry configured to measure the channel loading conditions and the amount of signal interference. This could be done by receiving a reference signal from computing system 15 with a known transmit power level. Microprocessor 30 compares the measured power level with the known transmit power level to determine the measured load. Based on the measured loading, microprocessor 30 adjusts the amount of amplification in transceiver 32 such that there is a higher probability of successful reception of the encoded data by computing system 15.

Figure 3B:
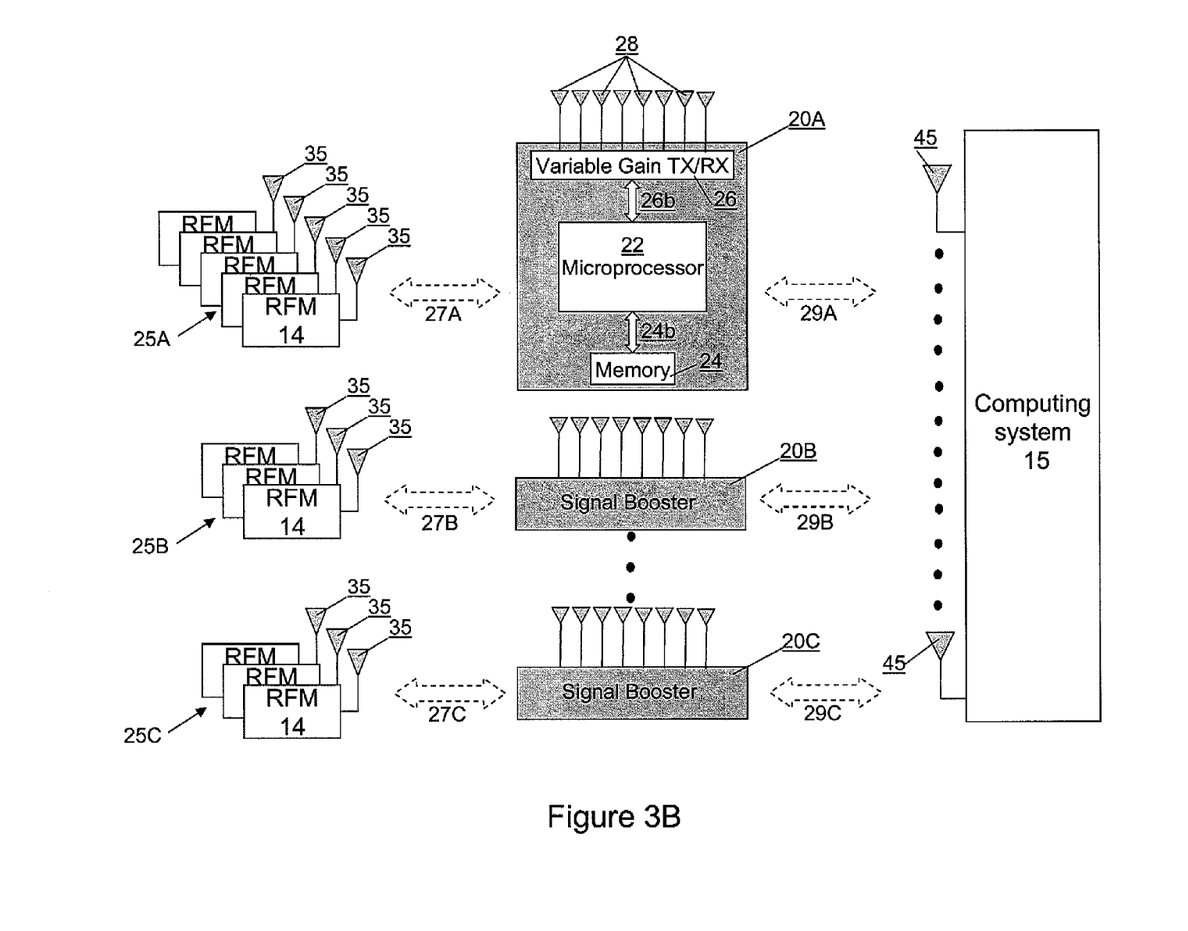
FIG. 3B illustrates an exemplary system containing groups of radio frequency modules communicatively linked to signal boosters.

In an alternate embodiment, to reduce costs or complexity of design the RFM's 14, the amplification range of module transceivers 32 is limited. FIG. 3B illustrates this alternative embodiment where multiple signal boosters 20A-20C are disposed at locations which could be internal or external to the structure. Each signal booster is capable of communicating with both a series of RFMs 14 and the computing system 15. Signal boosters 20A-20C are communicatively linked to groups 25A-25C of RFMs 14 respectively. Particularly, group 25A is communicatively linked to signal booster 20A, while groups 25B and 25C are communicatively linked to signal boosters 20B and 20C respectively. As also illustrated in FIG. 3B, each signal booster 20A-20C includes a plurality of antennas 28, a memory circuit 24, a variable gain transceiver 26 and a microprocessor 22.

By way of example, the operation of only signal booster 20A and associated RFM group 25A will be discussed in detail, but it is understood that the operation is identical in the other signal boosters 20B and 20C. Microprocessor 22 is operatively connected to memory 24 via memory bus 24b. Memory 24 can store various measurement results from one or more RFMs 14 within the group of RFMs 25A, but could also contain operational instructions used by microprocessor 22. Measured data from one or more sensors 34 within REM group 25A is provided to the variable gain transceiver 26 of signal booster 20A via wireless communication link 27A. Microprocessor 22 can perform any necessary processing to the measured data, such as data compression, correlating and formatting. The processed data is then sent to memory 24 via memory bus 24b for storage. However, it should be understood that the measured data from group RFM 25A could be sent directly to memory 24 without microprocessor 22 performing any processing. Microprocessor 22 is also capable of adjusting the gain of variable gain transceiver using methods similar to the one discussed above.

Figure 4:
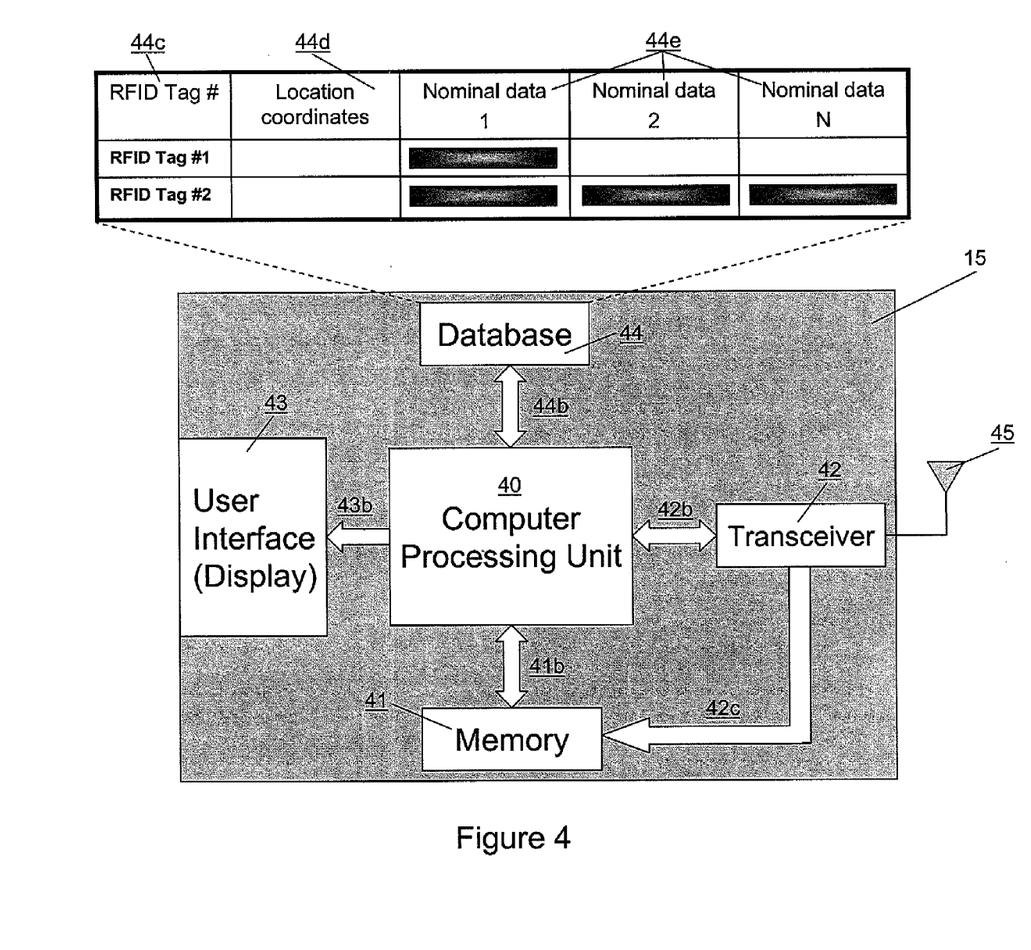
FIG. 4 illustrates an exemplary computing system.

An exemplary illustration of computing system 15 is shown in FIG. 4. Computing system 15 includes computer processing unit (CPU) 40, computing memory 41, database 44, user interface 43, and computing transceiver 42. CPU 40 is connected to computing memory 41, computing transceiver 42, user interface 43, and database 44 via buses 41b, 42b, 43b, and 44b respectively. In addition computing transceiver 42 is connected to computing memory 41 via bus 42c.

Computing memory 41 contains enough storage space to store the measurement results from all of the RFMs 14 in the monitoring system. Computing memory 41 can also contain operational instructions used by CPU 40 to control collection of measured data from RFMs 14. Measured data from RFMs 14 is received by computing transceiver 42 and is provided for storage in computing memory 41 via transceiver bus 42c. As with the individual microprocessors 30 contained on each RFM 14, CPU 40 can perform any necessary processing to the measured data provide by RFMs 14 and can control all the functionality and timing of the radio-frequency modules 14 within the monitoring system. However, CPU 40 is further configured to compare the measured data with the nominal data stored in database 44 in order to determine if a change in status has occurred. Accordingly, CPU 40 can be used to incorporate the comparison result into a three-dimensional model of the building for display on user interface 43.

By incorporating the measured data into a three-dimensional model a better understanding of the structural integrity of the building can be maintained. Further, if catastrophic events such as fires, earthquakes, weather events, or explosions cause structural integrity failures, the information provided in the displayed three-dimensional model could be invaluable to first responders trying to determine the safest way into the building.

The comparison of measured data to nominal data performed by CPU 40 could also provide information as to how the structural members 12 are behaving over time. This information could result in the user overwriting the values for the nominal data stored in database 44 to reflect normal changes that occur in structural members as building 10 settles over time.

An example showing how database 44 could be configured is shown in FIG. 4. Database 44 contains entries which correlate the unique RFID tag numbers 33 of each RFM 14 to a specific location within the building 10. In particular, FIG. 4 shows database 44 including columns containing a list of RFID tag numbers 44c, the location coordinates 44d corresponding to RFID tag numbers 44c secured to metal clips 13 within building 10, and nominal or expected data entries 44e corresponding to RFMs 14. One of ordinary skill would understand that the number of columns necessary for containing nominal or expected data entries is dependent on the required data to be compared with the RFMs 14. For example, FIG. 4 shows that RFID tag #1 is configured to measure one type of data, such as temperature. However, RFID tag #2 is configured to measure three types of data, such as temperature, stress and torque. Thus, the row in database 44 containing RFID tag #1 will only have data in a single column 44e, whereas the row in database 44 containing RFID tag #2 will have data in three separate columns 44e corresponding to the three types of measured data.

With the understanding of the apparatus used in the monitoring system, the following description will focus on how the above described system could be used. Those skilled in the art will appreciate, however, that the present description may be applied using other methods.

Figure 5:
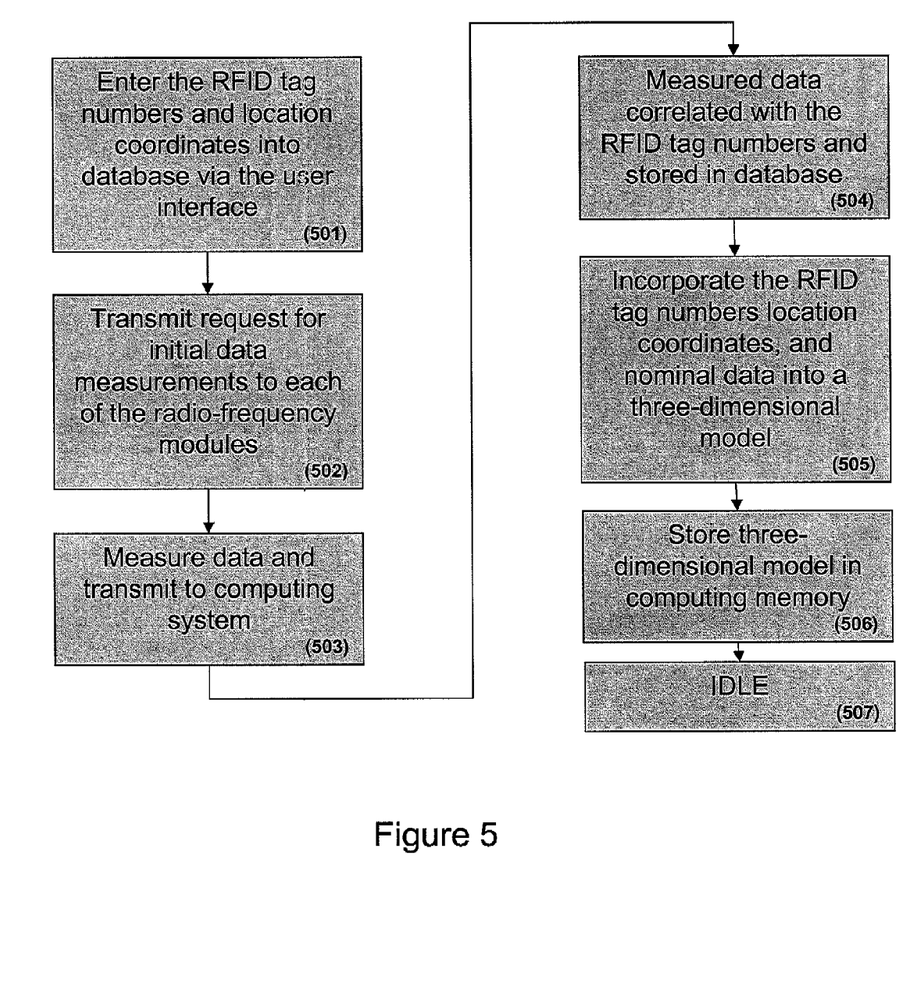
FIG. 5 illustrates an exemplary procedure to initialize a structural integrity monitoring system.

Before the monitoring system can be fully functional, the system needs to be initialized and nominal data must be stored in database 44. This process could be as simple as programming database 44 with the RFID tag numbers 44c, location coordinates 44d, and initial nominal data 44e. However, a preferred process for initializing the system is shown in detail in describing FIG. 5. The process starts (501) with the entering the RFID tag numbers 44c and location coordinates 44d into database 44 via the user interface 43. After the initial setup of database 44, computing system 15 is activated and transmits a request for initial data measurements (502) from each of the RFMs 14. The requests could be made serially or in parallel depending on the user's preference and communication protocol chosen. The process continues with the transmission of the measured data (503) from RFMs 14 to computing system 15, where the measured data is correlated with the RFID tag numbers 44c and stored in database 44 (504). In process step 505, CPU 40 incorporates the RFID tag numbers 44c, location coordinates 44d, and nominal data 44e into a three-dimensional model of building 10. The three-dimensional model is then stored in computing memory (506). After storing the initialization information the system is put into an idle state (507) where it awaits future data collection requests.

Future data collection requests could be triggered be any number of methods. For example computing system 15 could be configured to trigger data collection based on a predetermined schedule or an external request via user interface 43.

The computing system could also be programmed to remain idle unless one of the radio-frequency modules 14 indicates that a failure has occurred. For such a module based event to trigger a warning, module memory 31 must be provided with the expected nominal data stored in database 44 and microprocessor 30 must be programmed to periodically instruct one or more sensors 34 to measure data. Microprocessor 30 would perform the comparison of the measured data with the nominal data stored in module memory 31 and would only instruct module transceiver 32 to transmit the RFID tag 33 and the measured data in the event of a failure.

Figure 6:
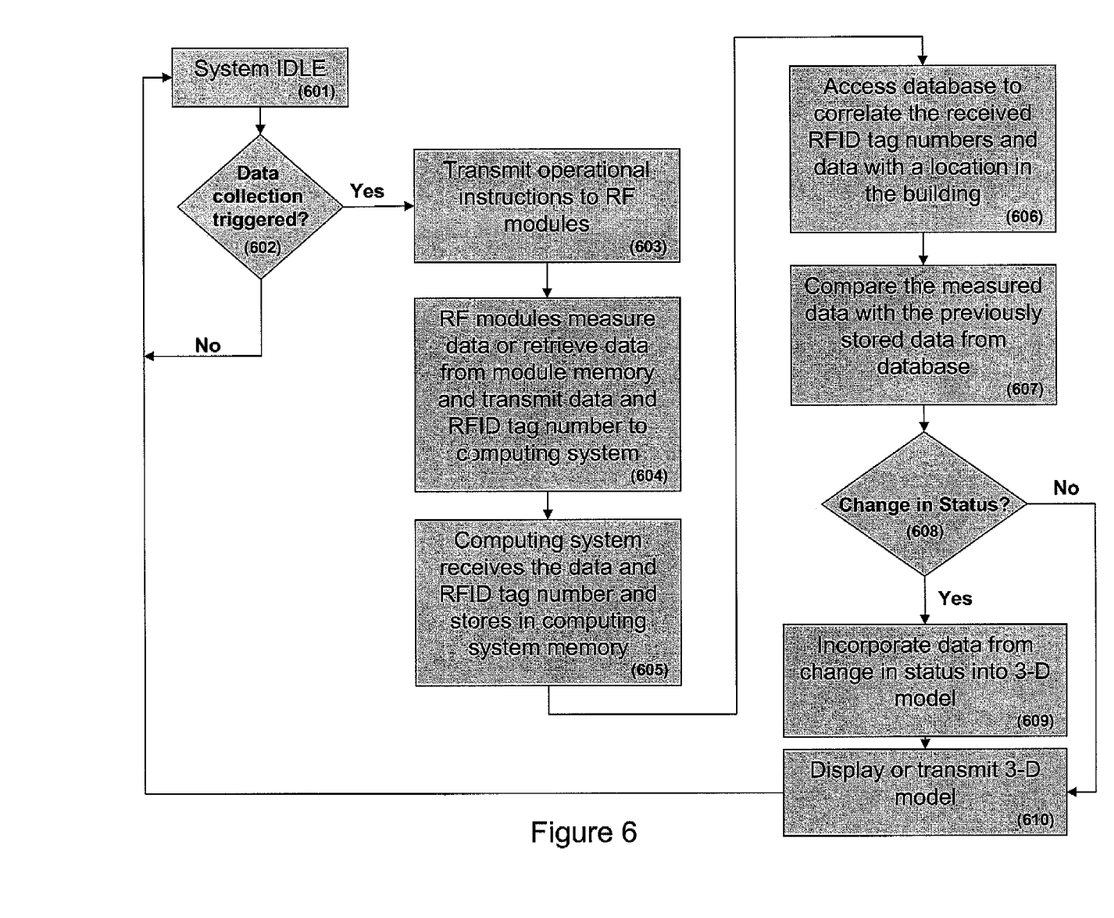
FIG. 6 illustrates an exemplary procedure used by a computer system to monitor the structural integrity of a building.

Another method for controlling the computing system is described in FIG. 6. This process starts with the computing system in an idle state (601). When a data collection triggering event occurs (602), computing system 15 transmits operational instructions to RFMs 14 using an encrypted communication protocol (603). Each radio-frequency module either measures the data directly or retrieves the previously stored data from module memory 31 and transmits the data and the RFID tag number 33 to computing system 15 (604). The process continues in process step 605, where the computing system 15 receives the measured data and RFID tag numbers 33 and stores the information in computing memory 41. Database 44 is accessed (606) to correlate the received RFID tag numbers 33 with the RFID tag numbers stored in 44c. This correlation is necessary to determine the location of the RFMs 14 within the building and ensure that the data comparison performed in process step 607 uses the correct nominal data. If a status change is detected (608) the newly measured data is incorporated into the three-dimensional model and is provided to the user interface 43 which displays the status changes (610). Assuming no change is status is detected, the previously stored three-dimensional model is displayed. Computing system 15 then returns to an idle state (601) where it awaits another data collection triggering event.

As previously mentioned, the protocol used for computing system 15 to communicate with the radio-frequency modules 14 could be a wireless local area network (WLAN) protocol, or a cellular mobile telephone system. An exemplary communication system used in the present invention relates to multiple access protocols and, more particularly, to an assignment-based multiple access protocol for an uplink channel having a plurality of subcarriers.

In a wireless packet data network, the plurality of radio-frequency modules 14 transmits packet data to computing system 15 over an uplink channel. The channel is typically divided in the time domain into a sequence of time slots. The radio-frequency modules 14 share the channel by transmitting in different sub-carrier frequencies. In such cases, multiple radio-frequency modules 14 may transmit in the same timeslot, but on different subcarrier frequencies.

Figure 7:
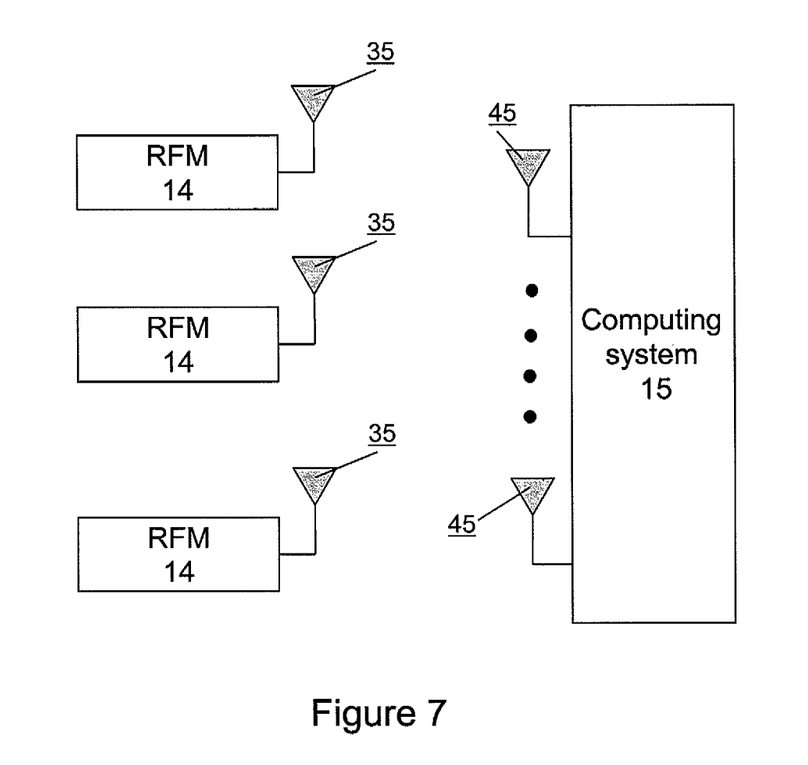
FIG. 7 illustrates an exemplary communication system for communication between the computing system and multiple radio-frequency modules.

Referring now back to the drawings, the communication system will be described in the context of an uplink channel. Those skilled in the art will appreciate, however, that the present invention could also be applied to many communication technologies, such as code division multiple access (CDMA) and time division multiple access (TDMA) systems. As shown in FIG. 7, the plurality of radio-frequency modules 14 communicates over an uplink channel with computing system 15. The computing system 15 has multiple receive antennas 45. Each radio-frequency module 14 has a single transmit antenna 35. Of course, it is understood that the communication system could be realized using communication technologies which use multiple channels without going beyond the scope of the invention.

Figure 8:
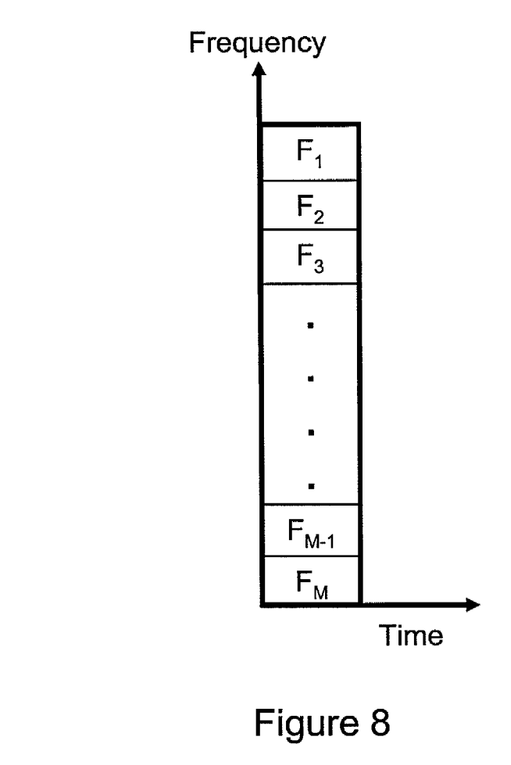
FIG. 8 illustrates an exemplary division of multiple sub-carrier frequencies transmitted and received in a given time slot.

The uplink channel is subdivided in the time domain into a plurality of time slots. As is well known in the art, the uplink channel is further divided in the frequency domain into a plurality of subcarriers, as shown in FIG. 8. Data is transmitted by a radio-frequency module 14 in a selected subcarrier slot and is spread across time. Access to the shared uplink channel is assignment-based. To access the channel, the computing system 15 selects each radio-frequency module 14 the transmit subcarrier frequency that will be used by the radio-frequency module 14 to transmit the measured data back to the computing system 15. The information transmitted by the radio-frequency module 14 over a time slot is referred to herein as a data packet.

In the exemplary embodiment, the computing system 15 employs multi-packet reception (MPR) to receive data packets from multiple radio-frequency modules 14 in a single time slot. Because the computing system 15 is equipped with multiple antennas 45, the computing system 15 can exploit spatial and multi-user diversity of the radio-frequency module 14 to jointly decode and demodulate data packets that are simultaneously transmitted from multiple radio-frequency modules 14. Assuming that each radio-frequency modules 14 spread the data packets over all of the available subcarriers, a computing system 15 having N receive antennas 45 could simultaneously demodulate and decode data packets from up to N radio-frequency modules 14.

Figure 9:
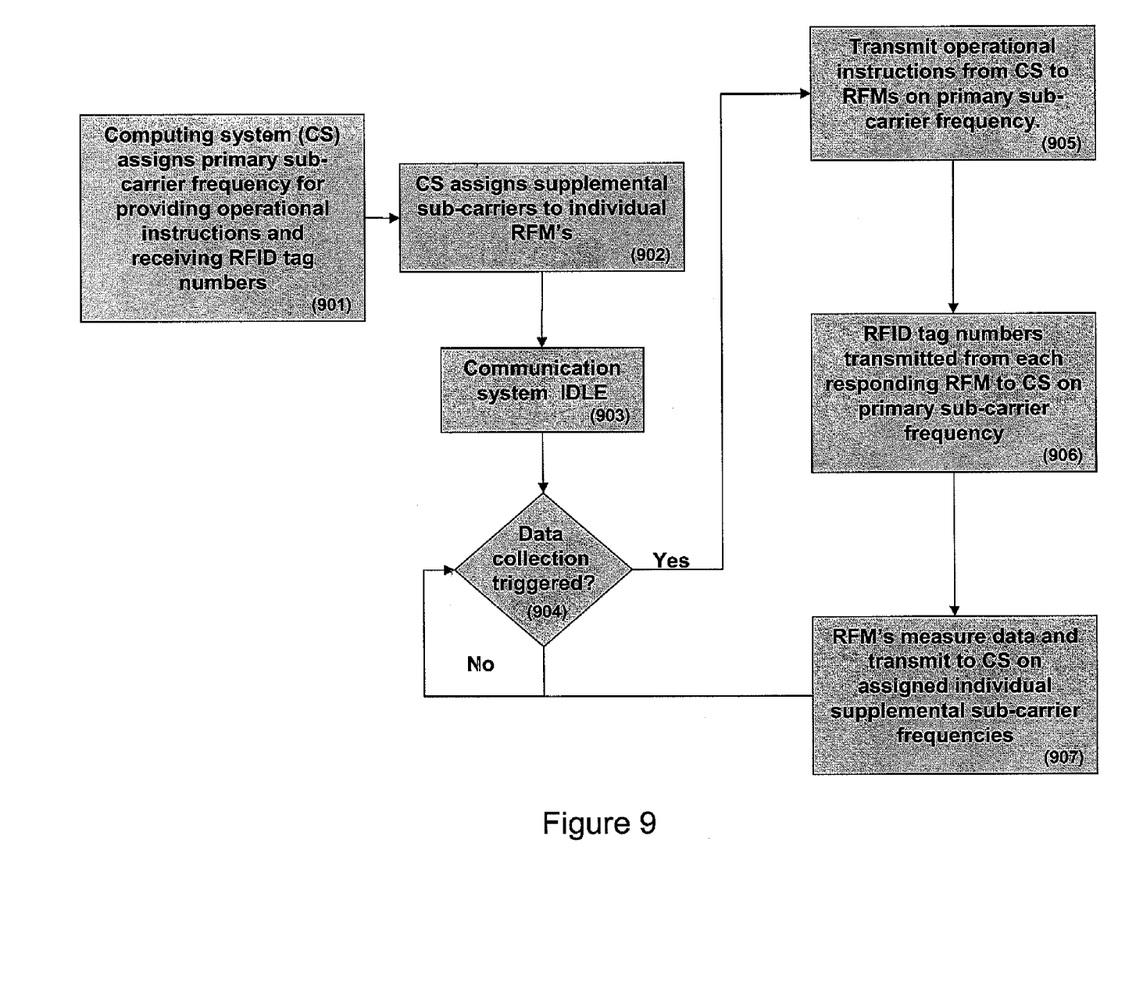
FIG. 9 illustrates an exemplary procedure for initializing and operating a communication system.

As previously discussed, the computing system 15 assigns each sub-carrier to each particular radio-frequency module. The assignment process can occur during the initialization of the system, as discussed with FIG. 5, or at any time during the normal operation of the monitoring system. FIG. 9 illustrates an exemplary process for communication between the computing system 15 and the various radio-frequency modules 14.

The communication protocol initialization starts with computing system 15 assigning a primary sub-carrier frequency for the exchange of operational instructions and the receiving of RFID tag numbers 44c (901). Once the primary sub-carrier frequency is assigned the computing system 15 assigns supplemental sub-carrier frequencies to each individual RFM 14 and communicates the supplemental sub-carrier frequency assignments to the RFMs 14 using the primary sub-carrier frequency in process step 902. After the communication protocol is established the system goes into an IDLE state (903) where it remains until a data collection event is triggered in process step 904. Once a data collection event is triggered, the process is much like the one described in FIG. 6, except that the process now has a defined communication protocol.

In detail, the process of data collection starts with the operational instructions being transmitted from the computing system 15 to the RFMs 14 on the primary sub-carrier frequency (905). The responding RFMs 14 communicate that they have received the operational instructions and respond on the primary sub-carrier frequency by transmitting the unique RFID tag number 33 (906). The computing system 15 receives the RFID tag numbers 33 and correlates them to the RFID tag numbers 44c stored in database 44. After measuring the data each RFM 14 transmits the measured data using only the supplemental subcarrier assigned in process step 902 to computing system 15. Multiple computing system antennas 45 receive the measured data, decode, and demodulate the measured data (907). The communication system returns to an IDLE state (904), where it awaits the next data collection event trigger.

The present invention may, of course, be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A system for monitoring the structural integrity of structural members of a building using radio-frequency identification tags with associated sensors comprising:
   a plurality of clips attached to respective structural members;
   a radio-frequency module secured to each of the clips and including:
      a radio-frequency identification tag identifiable via a unique tag number;
      a microprocessor device;
      a first memory;
      one or more sensors for measuring data related to the structural integrity of the structural members of buildings; and
      a transceiver capable of receiving operational instructions used to monitor the structural integrity of the building and transmitting the measured data; and
   a computing system configured to:
      transmit the operational instructions for collection of the measured data to the radio-frequency modules;
      receive the measured data from the radio-frequency modules;
      store the measured data in a second memory;
      process the measured data from the radio-frequency modules
      transmit the processed data via a communication protocol; and
   wherein the radio-frequency identification tag comprises an active radio-frequency identification tag, a passive radio-frequency identification tag, or a battery assisted passive radio-frequency identification tag.

2. The system of claim 1 wherein the computing system further includes a database that correlates the radio-identification tag number of each respective clip to a location in the building, the database capable of storing the measured data for each of the unique tag numbers for incorporation of the measured data into a three-dimensional model of the building.

3. The system of claim 2 wherein the computing system is further configured to display the three-dimensional model of the building including a graphical representation of the measured data within the three-dimensional model.

4. The system of claim 1 wherein the one or more sensors comprise strain gauges, temperature sensors, torque sensors, or pressure sensors.

5. The system of claim 1 wherein the operational instructions for collection of the measured data is triggered by a predetermined schedule, a sensor-based event or an external communication.

6. The system of claim 1, wherein the one or more sensors comprise strain gauges, temperature sensors, torque sensors, or pressure sensors;
   the operational instructions for collection of the measured data is triggered by a predetermined schedule, a sensor-based event or an external communication;
   the computing system further includes a database that correlates the radio-identification tag number of each respective clip to a location in the building, the database capable of storing the measured data for each of the unique tag numbers for incorporation of the measured data into a three-dimensional model of the building; and
   the computing system is further configured to display the three-dimensional model of the building including a graphical representation of the measured data within the three-dimensional model.

7. A system for creating a three-dimensional model and determining the structural integrity of structural members of buildings using radio-frequency identification tags with associated sensors comprising:
   a plurality of metal clips attached to respective structural members;
   a radio-frequency module secured to respective metal clips and including:
      a radio-frequency identification tag identifiable via a unique tag number;
      a microprocessor device;
      a first memory;
      one or more sensors for measuring data related to the structural integrity of the structural members of buildings; and
      a transceiver capable of receiving operational instructions used to monitor the structural integrity of the building and transmitting the measured data; and
   a computing system configured to:
      provide the operational instructions for collection of the measured data to the radio-frequency modules;
      receive the measured data from the radio-frequency modules;
      store the measured data in a second memory;
      process the measured data from the radio-frequency modules; and compare the measured data with a database that correlates the radio-frequency identification tag number from each respective clip to a location in the building, the database capable of comparing the measured data for each of the unique tag numbers with previously stored measured data and incorporating the differences into a three-dimensional model of the building;

provide a user interface which displays the three-dimensional model based on the measured data received from the radio-frequency modules; and transmit the processed data via a communication protocol.

8. The system of claim 7 wherein the one or more sensors comprises strain gauges, temperature sensors, torque sensors, or pressure sensors.

9. The system of claim 7 wherein the operational instructions for collection of the measured data is triggered by a predetermined schedule, a sensor-based event or a communication from the outside world.

10. The system of claim 7 wherein the three-dimensional model displayed on the user interface comprises displaying structural failures within the plurality of structural members within the building.

11. The system of claim 7 wherein the radio-frequency identification tag comprises an active radio-frequency identification tag, a passive radio-frequency identification tag, or a battery assisted passive radio-frequency identification tag.

12. The system of claim 7 wherein the operational instructions from the computing system and the measured data from each of the radio-frequency modules is transmitted in an encrypted format.

13. A method for monitoring the structural integrity of buildings using radio-frequency identification tags with associated sensors, the method comprising:

connecting a plurality of metal clips which are operatively associated with a plurality of radio-frequency modules to a plurality of structural members, each radio-frequency module including:
  a radio-frequency identification tag via a unique tag number;
  a microprocessor device;
  a memory;
  one or more sensors for measuring data related to the structural integrity of the structural members of buildings; and
  a transceiver capable of receiving operational instructions used to monitor the structural integrity of the building and transmitting the measured data; and monitoring the structural integrity of the buildings with a computer system by:
  transmitting the operational instructions to the of radio-frequency modules;
  receiving the measured data from the radio-frequency modules;
  storing the measured data;
  processing the measured data from the radio-frequency modules by:
    correlating the radio-frequency identification tag number with each respective clip to a location in the building;
    comparing the measured data with previously saved data to determine if a change in status has occurred;
    incorporating the comparison result into a three-dimensional model which reflects the structural integrity of the building
  providing the three-dimensional model to a display; and
  transmitting the processed data via a communication protocol.

14. The method of claim 13 wherein the transmitting the operational instructions from the computing system and transmitting the measured data from the radio-frequency modules is performed in an encrypted format.

15. The method of claim 13 wherein transmitting the operational instructions from a computer system to the radio-frequency modules and receiving radio-frequency identification tag numbers and measured data from the radio-frequency modules further comprises:

assigning a primary subcarrier for providing the operational instructions from the computer system to the radio-frequency modules and for transmitting the radio-frequency identification tag numbers for the radio-frequency identification tag;

receiving the radio-frequency identification tag numbers in an uplink timeslot on the assigned primary subcarrier assigned to the radio-frequency modules;

assigning supplemental subcarriers to individual radio-frequency modules for transmitting the measured data from the individual radio-frequency modules;

transmitting the supplemental subcarrier information in the operational instructions from the computer system to the radio-frequency modules;

receiving the measured data from the individual radio-frequency modules on the respective supplemental subcarrier selected by the computing system; and decoding and demodulating the measured data.

16. The method of claim 15 wherein the supplemental subcarrier selection information is transmitted to the radio-frequency modules on the primary subcarrier.

17. A system for monitoring the structural integrity of structural members of a building using radio-frequency identification tags with associated sensors comprising:

a plurality of radio-frequency modules, each radio-frequency module being secured to respective structural members and including:
  a radio-frequency identification tag identifiable via a unique tag number; a microprocessor device; a first memory; one or more sensors for measuring data related to the structural integrity of the structural members of buildings; and
  a transceiver capable of receiving operational instructions used to monitor the structural integrity of the building and transmitting the measured data; and a computing system configured to:
  transmit the operational instructions for collection of the measured data to the plurality of radio-frequency modules;
  receive the measured data from the plurality of radio-frequency modules; store the measured data in a second memory; process the measured data from the plurality of radio-frequency modules;
  transmit the processed data via a communication protocol; and
  wherein the radio-frequency identification tag comprises an active radio-frequency identification tag, a passive radio-frequency identification tag, or a battery assisted passive radio-frequency identification tag.

18. A system for monitoring the structural integrity of structural members of a building using radio-frequency identification tags with associated sensors comprising:

a plurality of clips attached to respective structural members;

a radio-frequency module secured to each of the clips and including:

a radio-frequency identification tag identifiable via a unique tag number;
a microprocessor device;
a first memory;
one or more sensors for measuring data related to the structural integrity of the structural members of buildings; and
a transceiver capable of receiving operational instructions used to monitor the structural integrity of the building and transmitting the measured data; and a computing system configured to:
  transmit the operational instructions for collection of the measured data to the radio-frequency modules;
  receive the measured data from the radio-frequency modules;
  store the measured data in a second memory;
  process the measured data from the radio-frequency modules;
  transmit the processed data via a communication protocol; and
wherein the operational instructions from the computing system and the measured data from each of the radio-frequency modules is transmitted in an encrypted format.

* * * * *